United States Patent
Sabelle et al.

(10) Patent No.: US 11,117,864 B2
(45) Date of Patent: Sep. 14, 2021

(54) USE FOR DYEING KERATIN FIBERS OF A COMPOUND OF AZOMETHINE TYPE BEARING A QUINOLINE-DERIVED UNIT

(71) Applicant: L'OREAL, Paris (FR)

(72) Inventors: Stéphane Sabelle, Aulnay-sous-Bois (FR); Aziz Fadli, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 145 days.

(21) Appl. No.: 16/310,974

(22) PCT Filed: Jun. 21, 2017

(86) PCT No.: PCT/EP2017/065249
§ 371 (c)(1),
(2) Date: Dec. 18, 2018

(87) PCT Pub. No.: WO2017/220658
PCT Pub. Date: Dec. 28, 2017

(65) Prior Publication Data
US 2020/0308117 A1 Oct. 1, 2020

(30) Foreign Application Priority Data
Jun. 23, 2016 (FR) ...................... 1655847

(51) Int. Cl.
| C07D 215/38 | (2006.01) |
| A61K 8/49 | (2006.01) |
| A61Q 5/06 | (2006.01) |
| C07D 471/04 | (2006.01) |
| C07D 487/04 | (2006.01) |

(52) U.S. Cl.
CPC .......... *C07D 215/38* (2013.01); *A61K 8/4926* (2013.01); *A61K 8/4946* (2013.01); *A61Q 5/065* (2013.01); *C07D 471/04* (2013.01); *C07D 487/04* (2013.01); *A61K 2800/4322* (2013.01)

(58) Field of Classification Search
CPC .... A61K 8/4926; A61K 8/4946; A61Q 5/065; C07D 471/04; C07D 487/04
See application file for complete search history.

(56) References Cited

U.S. PATENT DOCUMENTS

| 3,972,937 | A | * | 8/1976 | Kalopissis | ............. A61K 8/413 |
| | | | | | 562/585 |
| 4,003,699 | A | | 1/1977 | Rose et al. | |
| RE30,199 | E | | 1/1980 | Rose et al. | |
| 5,061,289 | A | | 10/1991 | Clausen et al. | |
| 5,221,658 | A | * | 6/1993 | Bach | ........................ B41M 5/39 |
| | | | | | 428/913 |
| 5,380,340 | A | | 1/1995 | Neunhoeffer et al. | |
| 5,534,267 | A | | 7/1996 | Neunhoeffer et al. | |
| 5,663,366 | A | | 9/1997 | Neunhoeffer et al. | |
| 5,708,151 | A | | 1/1998 | Mockli | |
| 5,766,576 | A | | 6/1998 | Lowe et al. | |
| 5,792,221 | A | | 8/1998 | Lagrange et al. | |
| 6,099,592 | A | | 8/2000 | Vidal et al. | |
| 6,099,593 | A | | 8/2000 | Terranova et al. | |
| 6,284,003 | B1 | | 9/2001 | Rose et al. | |
| 6,884,265 | B2 | | 4/2005 | Vidal et al. | |
| 7,060,110 | B2 | | 6/2006 | Vidal et al. | |
| 7,887,601 | B2 | | 2/2011 | Fadli et al. | |
| 2002/0095732 | A1 | | 7/2002 | Kravtchenko et al. | |
| 2003/0106169 | A1 | | 6/2003 | Vidal et al. | |
| 2004/0107513 | A1 | | 6/2004 | Vidal et al. | |
| 2004/0127692 | A1 | | 7/2004 | David et al. | |
| 2004/0143911 | A1 | | 7/2004 | Vidal | |
| 2004/0168263 | A1 | | 9/2004 | Vidal | |
| 2005/0039268 | A1 | | 2/2005 | Plos et al. | |
| 2007/0136959 | A1 | | 6/2007 | Fadli | |

(Continued)

FOREIGN PATENT DOCUMENTS

| DE | 2359399 A1 | 6/1975 |
| DE | 3843892 A1 | 6/1990 |
| DE | 4133957 A1 | 4/1993 |
| DE | 19543988 A1 | 5/1997 |
| EP | 0714954 A2 | 6/1996 |
| EP | 0770375 A1 | 5/1997 |
| EP | 1792606 A1 | 6/2007 |
| EP | 1792903 A1 | 6/2007 |
| EP | 2246038 A1 | 11/2010 |
| FR | 2692572 A1 | 12/1993 |
| FR | 2733749 A1 | 11/1996 |

(Continued)

OTHER PUBLICATIONS

Dorwald; "Side Reactions in Organic Synthesis a Guide to Successful Synthesis Design", Wiley-VCH, 2005, Preface and Chapter 1 ; 32 Pages. (Year: 2005).*

(Continued)

*Primary Examiner* — Daniel R Carcanague
(74) *Attorney, Agent, or Firm* — The Marbury Law Group, PLLC

(57) ABSTRACT

The invention relates to a compound chosen from the compounds of formula (I) below, the optical and geometrical isomers thereof and the tautomers thereof, and also the addition salts thereof with an acid or a base, and the solvates thereof: (I). The invention also relates to the use of these particular compounds and the compositions for dyeing keratin fibers.

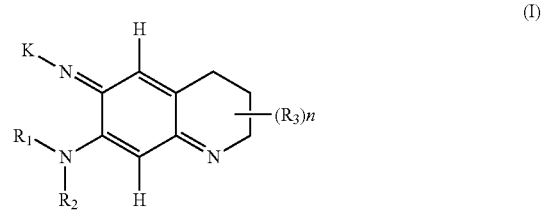

(I)

17 Claims, No Drawings

(56) References Cited

U.S. PATENT DOCUMENTS

2007/0143935 A1 6/2007 Fadli et al.
2010/0263139 A1 10/2010 Daubresse et al.

FOREIGN PATENT DOCUMENTS

| | | |
|---|---|---|
| FR | 2750048 A1 | 12/1997 |
| FR | 2807650 A1 | 10/2001 |
| FR | 2822693 A1 | 10/2002 |
| FR | 2822694 A1 | 10/2002 |
| FR | 2822696 A1 | 10/2002 |
| FR | 2822698 A1 | 10/2002 |
| FR | 2825625 A1 | 12/2002 |
| FR | 2825702 A1 | 12/2002 |
| FR | 2829926 A1 | 3/2003 |
| FR | 2844269 A1 | 3/2004 |
| FR | 2920778 A1 | 3/2009 |
| FR | 2983710 A1 | 6/2013 |
| FR | 3006181 A1 | 12/2014 |
| FR | 3006182 A1 | 12/2014 |
| GB | 1026978 A | 4/1966 |
| GB | 1153196 A | 5/1969 |
| JP | 02-019576 A | 1/1990 |
| JP | 05-163124 A | 6/1993 |
| WO | 94/08969 A1 | 4/1994 |
| WO | 94/08970 A1 | 4/1994 |
| WO | 95/01772 A1 | 1/1995 |
| WO | 95/15144 A1 | 6/1995 |
| WO | 96/15765 A1 | 5/1996 |
| WO | 02/078660 A1 | 10/2002 |
| WO | 02/100369 A2 | 12/2002 |
| WO | 02/100834 A1 | 12/2002 |
| WO | 2013/087768 A1 | 6/2013 |

OTHER PUBLICATIONS

International Search Report for counterpart Application No. PCT/EP2017/065249, dated Aug. 11, 2017.

\* cited by examiner

USE FOR DYEING KERATIN FIBERS OF A COMPOUND OF AZOMETHINE TYPE BEARING A QUINOLINE-DERIVED UNIT

CROSS REFERENCE TO RELATED APPLICATIONS

This is a national stage application of PCT/EP2017/065249, filed internationally on Jun. 21, 2017, which claims priority to French Application No. 1655847, filed on Jun. 23, 2016, both of which are incorporated by reference herein in their entireties.

The present invention relates to novel compounds of azomethine type bearing a quinoline-derived unit and to the use thereof for dyeing keratin fibers, and in particular human keratin fibers such as the hair, and also to a process for treating keratin fibers using said compounds.

It is known practice to dye keratin fibers with dye compositions containing direct dyes. These compounds are colored and coloring molecules that have affinity for the fibers. It is known practice, for example, to use direct dyes of the nitrobenzene type, anthraquinone or nitropyridine dyes, and dyes of the azo, xanthene, acridine, azine or triarylmethane type.

These dyes are usually applied to fibers optionally in the presence of an oxidizing agent, if it is desired to obtain simultaneous lightening of the fibers. Once the leave-on time has elapsed, the fibers are rinsed, optionally washed and dried.

The colorings resulting from the use of direct dyes are colorings that are often chromatic but are, however, only temporary or semi-permanent since the nature of the interactions that bind the direct dyes to the keratin fiber and their desorption from the surface and/or the core of the fiber are responsible for their weak dyeing power and their poor relative persistence with respect to washing or perspiration. These direct dyes are also generally light-sensitive since the resistance of the chromophore to photochemical attack is low, leading to fading or a color change of the coloring of the hair over time. The sensitivity of these dyes to light depends on their uniform distribution or their distribution as aggregates in and/or on the keratin fiber.

There is therefore still progress to be made in this field in order to provide novel compositions for dyeing human hair which make it possible to obtain powerful new shades, in particular blues, which exhibit good uptake on the hair and good resistance to external attacks.

In addition, some direct dyes are used as a "bleaching booster" in bleaching mixtures comprising oxidizing agents such as persalts and/or hydrogen peroxide, so as to neutralize the background lightening of the hair fiber and to adjust the final color obtained, and to prevent the color changing to orangey or yellow shades.

In the context of this use, direct dyes compatible with these oxidizing agents, having good stability in their presence, are thus sought.

The aim of the present invention is to provide novel direct dyes for dyeing keratin fibers which have improved dyeing properties and good compatibility with the oxidizing agents.

In particular, one of the aims of the present invention is to provide direct dyes enabling good uptake on the hair fiber, that make it possible to obtain a strong, chromatic, esthetic, sparingly selective coloring with varied shades, which shows good resistance to the various attacking factors to which the hair may be subjected such as shampoos, light, sweat and permanent reshaping, and which are stable in the presence of oxidizing agents.

The Applicant has thus discovered, surprisingly, that particular compounds chosen from dyes of azomethine type derived from quinoline of formula (I) as defined below, the optical isomers, geometrical isomers and tautomers thereof, the addition salts thereof with an acid or a base and the solvates thereof such as hydrates make it possible to achieve this aim.

More specifically, a subject of the present invention is compounds of formula (I) below, the optical isomers, geometrical isomers and tautomers thereof, and also the addition salts thereof with an acid or a base, and the solvates thereof:

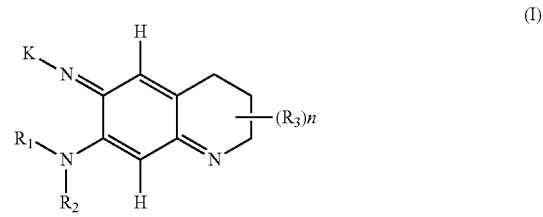

wherein:

n represents an integer equal to 0, 1, 2, 3, 4, 5 or 6, preferably equal to 0, it being understood that the positions not substituted with a radical $R_3$ carry a hydrogen atom, $R_1$ and $R_2$ independently represent
  a hydrogen atom
  a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, and $C_1$-$C_6$ alkylpiperidinium An⁻;

$R_1$ and $R_2$ can form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals, which may be identical or different, chosen from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium An⁻, $C_1$-$C_6$ alkylimidazolium An⁻, $C_1$-$C_6$ alkylpyridinium An or linear or branched $C_1$-$C_6$ alkyl, $R_3$ represents:
  a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, and $C_1$-$C_6$ alkylpiperidinium An⁻;

K represents a radical corresponding to general formulae (II) to (IV) below:

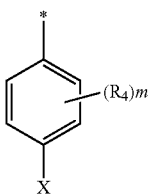

(II)

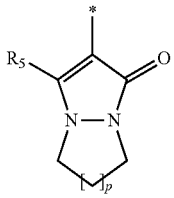

(III)

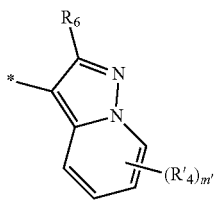

(IV)

wherein:
- m represents an integer equal to 0, 1, 2, 3 or 4, preferably equal to 0, 1 or 2, it being understood that the positions not substituted with a radical $R_4$ carry a hydrogen atom,
- m' represents an integer equal to 0, 1, 2, 3 or 4, preferably equal to 0, it being understood that the positions not substituted with a radical $R'_4$ carry a hydrogen atom,
- p represents an integer equal to 0, 1, 2, 3 or 4, preferably equal to 1 or 2,
- $R_4$ represents:
  - a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, and $C_1$-$C_6$ alkylpiperidinium An$^-$;
  - a linear or branched $C_1$-$C_6$ alkoxy radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, and $C_1$-$C_6$ alkylpiperidinium An$^-$;
  - a halide,
- $R'_4$ represents:
  - a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, and $C_1$-$C_6$alkylpiperidinium An$^-$;
  - a linear or branched $C_1$-$C_6$ alkoxy radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, and $C_1$-$C_6$ alkylpiperidinium An$^-$;
  - a halide,
- $R_5$ represents:
  - a hydrogen atom,
  - a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, and $C_1$-$C_6$alkylpiperidinium An$^-$;
  - a linear or branched $C_1$-$C_6$ alkoxy radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, and $C_1$-$C_6$alkylpiperidinium An$^-$;
  - a halide,
  - a hydroxyl radical,
  - a radical —$NR_7R_8$, wherein $R_7$ and $R_8$ independently represent:
    - a hydrogen atom,
    - a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, and $C_1$-$C_6$alkylpiperidinium An$^-$;
  - $R_7$ and $R_8$ can form, together with the nitrogen to which they are attached, a cationic or non-cationic, 4- to 7-membered, heterocycle which may contain one or more nitrogen, oxygen or sulfur atoms and which may itself be substituted with one or more radicals, which may be identical or different, chosen from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium or linear or branched $C_1$-$C_6$ alkyl,
- $R_6$ represents:
  - a hydrogen atom
  - a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, and $C_1$-$C_6$alkylpiperidinium An$^-$;
  - a linear or branched $C_1$-$C_6$ alkoxy radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, and $C_1$-$C_6$alkylpiperidinium An$^-$;
  - a halide,
  - a hydroxyl radical,
  - a radical —$NR_9R_{10}$, wherein $R_9$ and $R_{10}$ independently represent
  a hydrogen atom
  a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium $An^-$, $C_1$-$C_6$ alkylimidazolium $An^-$, $C_1$-$C_6$ alkylpyridinium $An^-$, $C_1$-$C_6$ alkylpiperidinium $An^-$, and linear or branched $C_1$-$C_6$ alkyl $R_9$ and $R_{10}$ can form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals, which may be identical or different, chosen from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium or linear or branched $C_1$-$C_6$ alkyl, X represents:
  a hydroxyl radical,
  a linear or branched $C_1$-$C_6$ alkoxy radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium $An^-$, $C_1$-$C_6$ alkylimidazolium $An^-$, $C_1$-$C_6$ alkylpyridinium $An^-$, and $C_1$-$C_6$ alkylpiperidinium $An^-$;
  a radical —$NR_{11}R_{12}$,
    wherein $R_{11}$ and $R_{12}$ independently represent
    a hydrogen atom
    a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, linear or branched $C_1$-$C_6$ alkyl, $C_1$-$C_6$ alkylimidazole, $C_1$-$C_6$ tri(hydroxy)alkylammonium $An^-$, $C_1$-$C_6$ alkylimidazolium $An^-$, $C_1$-$C_6$ alkylpyridinium $An^-$, and $C_1$-$C_6$ alkylpiperidinium $An^-$;
    $R_{11}$ and $R_{12}$ can form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals, which may be identical or different, chosen from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium or linear or branched $C_1$-$C_6$ alkyl, it being understood that when the compound of formula (I) is positively charged, then it comprises as many anionic counterion(s) $An^-$ as cationic charge(s) to achieve the electrical neutrality of the molecule.

The compounds according to the invention, as defined above, are useful for dyeing keratin fibers. They make it possible to obtain a coloring with varied, powerful, chromatic, esthetic, not very selective shades. In addition, the colorings obtained using the dyes (I) exhibit good fastness and withstand the various attacking factors to which hair may be subjected, such as shampoo, light, sweat and permanent reshaping.

A subject of the present invention is also the use of at least one of these compounds chosen from the compounds of formula (I) as defined in the present invention, the optical isomers, geometrical isomers and tautomers thereof, and also the addition salts thereof with an acid or a base and the solvates thereof, for dyeing keratin fibers, in particular human keratin fibers such as the hair.

Another subject of the invention is a composition for dyeing keratin fibers, comprising, in a medium that is suitable for dyeing, at least one compound according to the invention.

A subject of the present invention is also a process for dyeing keratin fibers using such a composition.

Other subjects, characteristics, aspects and advantages of the invention will emerge even more clearly on reading the description and the examples that follow.

In the text hereinbelow, and unless otherwise indicated, the limits of a range of values are included in that range, in particular in the expressions "between" and "ranging from . . . to . . . ".

The expression "at least one" used in the present description is equivalent to the expression "one or more".

In the context of the invention, unless otherwise mentioned, the term "alkyl radical" is intended to mean linear or branched alkyl radicals.

The saturated or unsaturated and optionally fused rings can also be optionally substituted.

The alkyl radicals are saturated, linear or branched, generally $C_1$-$C_{10}$ and particularly $C_1$-$C_{10}$ hydrocarbon-based radicals, preferably $C_1$-$C_6$ alkyl radicals, such as methyl, ethyl, propyl, butyl, pentyl and hexyl.

The alkenyl radicals are unsaturated, linear or branched $C_2$-$C_{10}$ hydrocarbon-based radicals, comprising at least one double bond, particularly $C_2$-$C_6$ alkenyl radicals such as ethylene, propylene, butylene, pentylene, 2-methylpropylene and decylene.

The alkynyl radicals are unsaturated, linear or branched $C_2$-$C_{10}$ hydrocarbon-based radicals, comprising at least one triple bond, particularly $C_2$-$C_6$ alkynyl radicals.

The alkoxy radicals are alkyl-oxy radicals with alkyl as defined above, preferably $C_1$-$C_{10}$ alkyl, such as methoxy, ethoxy, propoxy and butoxy.

The alkoxyalkyl radicals are preferably ($C_1$-$C_{20}$)alkoxy($C_1$-$C_{20}$)alkyl radicals, such as methoxymethyl, ethoxymethyl, methoxyethyl and ethoxyethyl.

For the purposes of the present invention, the term "interrupted" is intended to mean that the alkyl group is interrupted on the carbon-based chain of said alkyl with one or more heteroatoms. Examples that may be mentioned include -Ak-O-Ak", -Ak-N(R)-Ak", -Ak-O-Ak'-N(R)-Ak", -Ak-N(R)-Ak'-N(R)-Ak" or -Ak-O-Ak'-O-Ak", with Ak and Ak' representing $C_1$-$C_4$ alkylene groups and Ak" representing a $C_1$-$C_4$ alkyl group.

The halogens are preferably chosen from fluorine, chlorine, bromine and iodine atoms.

The "alkylcarbonyl" radicals are alkyl-carbonyl radicals with alkyl as defined previously, preferably $C_1$-$C_{10}$ alkyl, such as acetyl.

The "alkoxycarbonyl" radicals are —O—C(0)-alkyl radicals with alkyl as defined previously, for instance acetate, propionate, citrate, tartrate, gluconate and lactate.

The "alkyl", "alkenyl", "cyclic" and "cycloalkyl" radicals, when they are substituted, are substituted with at least one substituent borne by at least one carbon atom, chosen from 1) a halogen atom, a group chosen from 2) hydroxyl; 3) oxo; 4) $C_1$-$C_2$ alkoxy; 5) $C_1$-$C_{10}$ alkoxycarbonyl; 6) $C_1$-$C_{10}$ alkyl carbonyl; 7) (poly)hydroxy($C_2$-$C_4$)alkyl; 8)

(poly)hydroxy($C_2$-$C_4$)alkoxy; 9) amino; 10) quaternary ammonium —$N^+R'R''R'''$, $M^-$ for which R', R" and R''', which may be identical or different, represent a hydrogen atom or a $C_1$-$C_4$ alkyl group; and $M^-$ represents an anionic counterion, in particular a halide; 11) 5- or 6-membered heterocycloalkyl; 12) optionally cationic 5- or 6-membered heteroaryl, preferentially imidazolium, optionally substituted with a ($C_1$-$C_4$)alkyl radical, preferentially methyl; 13) amino substituted with one or two identical or different $C_1$-$C_6$ alkyl radicals optionally bearing at least: i) a hydroxyl group, ii) amino optionally substituted with one or two $C_1$-$C_3$ alkyl radicals, it being possible for said alkyl radicals to form, with the nitrogen atom to which they are attached, a saturated or unsaturated 5- to 7-membered heterocycle optionally comprising at least one other nitrogen or non-nitrogen heteroatom, iii) quaternary ammonium —$N^+R'R''R'''$, $M^-$ for which R', R" and R''', which may be identical or different, represent a hydrogen atom or a $C_1$-$C_4$ alkyl group; and $M^-$ represents an anionic counterion, in particular a halide, iv) optionally cationic 5- or 6-membered heteroaryl, preferentially imidazolium, optionally substituted with a $C_1$-$C_4$ alkyl radical, preferentially methyl; 14) acylamino (—NR—C(O)—R') wherein the radical R is a hydrogen atom or a $C_1$-$C_4$ alkyl radical optionally bearing at least one hydroxyl group and the radical R' is a $C_1$-$C_2$ alkyl radical; 15) carbamoyl (($R)_2$N—C(O)—) wherein the radicals R, which may be identical or different, represent a hydrogen atom or a $C_1$-$C_4$ alkyl radical optionally bearing at least one hydroxyl group; 16) alkylsulfonylamino (R'S(O)$_2$—N(R)—) wherein the radical R represents a hydrogen atom or a $C_1$-$C_4$ alkyl radical optionally bearing at least one hydroxyl group and the radical R' represents a $C_1$-$C_4$ alkyl radical, a phenyl radical; 17) aminosulfonyl (($R)_2$N—S(O)$_2$—) wherein the radicals R, which may be identical or different, represent a hydrogen atom or a $C_1$-$C_4$ alkyl radical optionally bearing at least one hydroxyl group; 18) carboxyl in acid or salified form (preferably salified with an alkali metal or a substituted or unsubstituted ammonium); 19) cyano; 20) nitro; 21) nitroso; 22) phenoxy optionally substituted with one or more hydroxyl groups; 23) phenylcarbonyloxy optionally substituted with one or more hydroxyl groups; 24) phenyloxycarbonyl optionally substituted with one or more hydroxyl groups; and 25) a phenyl group optionally substituted with one or more hydroxyl groups.

The "aryl", "heterocyclic" or "heteroaryl" radicals or the aryl, heteroaryl or heterocyclic part of the radicals, when they are substituted, are substituted with at least one substituent borne by at least one carbon atom, chosen from: 1) halogen; 2) $C_1$-$C_{10}$ alkyl, preferably $C_1$-$C_8$ alkyl, optionally substituted with one or more radicals chosen from the following radicals: i) hydroxyl, ii) $C_1$-$C_2$ alkoxy, iii) (poly)hydroxy($C_2$-$C_4$)alkoxy, iv) acylamino, v) amino substituted with two identical or different $C_1$-$C_4$ alkyl radicals optionally bearing at least one hydroxyl group or it being possible for the two radicals to form, with the nitrogen atom to which they are attached, a saturated or unsaturated 5- to 7-membered, preferably 5- or 6-membered, heterocycle optionally comprising another nitrogen or non-nitrogen heteroatom; 3) hydroxyl; 4) $C_1$-$C_2$ alkoxy; 5) $C_1$-$C_{10}$ alkoxycarbonyl; 6) $C_1$-$C_{10}$ alkylcarbonyloxy; 7) (poly)hydroxy($C_2$-$C_4$)alkyl; 8) amino; 9) 5- or 6-membered heterocycloalkyl; 10) optionally cationic 5- or 6-membered heteroaryl, preferably imidazolium, optionally substituted with a ($C_1$-$C_4$)alkyl radical, preferentially methyl; 11) amino substituted with one or two identical or different $C_1$-$C_6$ alkyl radicals optionally bearing at least: i) hydroxyl, ii) amino optionally substituted with one or two $C_1$-$C_3$ alkyl radicals, it being possible for said alkyl radicals to form, with the nitrogen atom to which they are attached, a saturated or unsaturated 5- to 7-membered heterocycle optionally comprising at least one other nitrogen or non-nitrogen heteroatom, iii) quaternary ammonium —$N^+R'R''R'''$, $M^-$ for which R', R" and R''', which may be identical or different, represent a hydrogen atom or a $C_1$-$C_4$ alkyl group; and $M^-$ represents an anionic counterion, in particular a halide, iv) optionally cationic 5- or 6-membered heteroaryl, preferentially imidazolium, optionally substituted with a $C_1$-$C_4$ alkyl radical, preferentially methyl; 12) quaternary ammonium —$N^+R'R''R'''$, $M^-$ for which R', R", R''' and $M^-$ are as defined previously; 13) acylamino (—N(R)—C(O)—R') wherein the radical R is a hydrogen atom or a $C_1$-$C_4$ alkyl radical optionally bearing at least one hydroxyl group and the radical R' is a $C_1$-$C_2$ alkyl radical; 14) carbamoyl (($R)_2$N—C(O))—) wherein the radicals R, which may be identical or different, represent a hydrogen atom or a $C_1$-$C_4$ alkyl radical optionally bearing at least one hydroxyl group; 15) alkylsulfonylamino (R'S(O)$_2$—N(R)—) wherein the radical R represents a hydrogen atom or a $C_1$-$C_4$ alkyl radical optionally bearing at least one hydroxyl group and the radical R' represents a $C_1$-$C_4$ alkyl radical, a phenyl radical; 16) aminosulfonyl (($R)_2$N—S(O)$_2$—) wherein the radicals R, which may be identical or different, represent a hydrogen atom or a $C_1$-$C_4$ alkyl radical optionally bearing at least one hydroxyl group; 17) carboxyl in acid or salified form (preferably salified with an alkali metal or a substituted or unsubstituted ammonium); 18) cyano; 19) nitro; 20) nitroso; 21) polyhaloalkyl, preferentially trifluoromethyl; 22) carboxyl; 23) phenylcarbonyloxy optionally substituted with one or more hydroxyl groups; 24) phenyloxycarbonyl optionally substituted with one or more hydroxyl groups; 25) phenyl optionally substituted with one or more hydroxyl or alkoxy groups; and 26) phenoxy.

The term "optionally substituted amino" radical is intended to mean an amino group which may bear one or two 1) identical or different $C_1$-$C_6$ alkyl radicals optionally bearing at least: i) a hydroxyl group, ii) an amino group optionally substituted with one or two $C_1$-$C_3$ alkyl radicals, said alkyl radicals or the two alkyl radicals form, with the nitrogen atom to which they are attached, a saturated or unsaturated, optionally substituted 5- to 7-membered heterocycle optionally comprising at least one other nitrogen or non-nitrogen heteroatom; 2) —C(O)(alkyl), the alkyl group possibly being substituted; 3) —C(O)O(alkyl), the alkyl group possibly being substituted; 4) —C(O)NH(alkyl), the alkyl group possibly being substituted; 5) —SO$_2$(alkyl), the alkyl group possibly being substituted.

The "cyclic" radicals are fused or non-fused, saturated or unsaturated, aromatic or non-aromatic monocyclic or polycyclic radicals, comprising from 4 to 30 carbon ring members, preferentially from 5 to 15 carbon atoms, optionally substituted with one or more atoms or groups as defined previously, in particular one or more alkyl, alkoxy, carboxyl, hydroxyl, amine or oxo groups.

The "aryl" radicals are fused or non-fused, monocyclic or polycyclic carbon-based radicals, preferentially comprising from 6 to 20 carbon atoms, and of which at least one ring is aromatic; preferentially chosen from phenyl, biphenyl, naphthyl, indenyl, anthracenyl and tetrahydronaphthyl radicals; more preferentially, the aryl radicals of the invention are phenyl radicals.

The "heterocyclic" radicals are fused or non-fused, saturated or unsaturated, aromatic or non-aromatic monocyclic or polycyclic, optionally cationic, 4- to 30-membered, preferentially 5- to 15-membered radicals, in at least one ring at least one ring member is a heteroatom, chosen in particular from O, N and S, preferably comprising from 1 to 6 heteroatoms, in particular O or N, optionally substituted with one or more atoms or groups as defined previously, in particular one or more alkyl, alkoxy, carboxyl, hydroxyl, amine or oxo groups.

When the heterocycle is cationic, then it bears a cationic charge inside the ring (endocyclic) or outside the ring (exocyclic), i.e. the heterocycle is substituted with a cationic group.

The "heteroaryl" radicals are fused or non-fused, preferentially 5- to 22-membered monocyclic or polycyclic radicals, comprising from 1 to 6 heteroatoms chosen from nitrogen, oxygen and sulfur atoms, and at least one ring of which is aromatic; preferentially, the heteroaryl radicals are chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrilyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthyl and the ammonium salts thereof.

Among the heterocyclic radicals that may be used in the invention, mention may be made particularly of furyl, pyranyl, pyrrolyl, piperazinyl, piperidyl, morpholinyl, imidazolyl, pyrazolyl, pyridyl and thienyl groups. Preferably, the heterocyclic groups are fused heteroaryl groups such as benzofuryl, chromenyl, xanthenyl, indolyl, isoindolyl, quinolyl, isoquinolyl, chromanyl, isochromanyl, indolinyl, isoindolinyl, coumarinyl or isocoumarinyl groups, these groups possibly being substituted, in particular with one or more non-adjacent hydroxyl groups.

The "heterocycloalkyl" radicals are saturated heterocyclic radicals as defined previously, such as tetrahydrofuryl, tetrahydropyranyl, piperazinyl, piperidyl or morpholinyl.

The cycloalkyl radicals are cyclic radicals as defined previously, preferably saturated $C_4$-$C_8$, monocyclic radicals, such as cyclobutyl, cyclopentyl or cyclohexyl. The cycloalkyl radicals may be substituted, in particular with alkyl, alkoxy, carboxylic acid, hydroxyl, amine and ketone groups.

The term "anionic counterion" is intended to mean an anion or an anionic group derived from an organic or mineral acid salt which counterbalances the cationic charge of the dye; more particularly, the anionic counterion is chosen from: i) halides such as chloride or bromide; ii) nitrates; iii) sulfonates, including $C_1$-$C_6$ alkylsulfonates: Alk-$S(O)_2O^-$ such as methanesulfonate or mesylate and ethanesulfonate; iv) arylsulfonates: Ar-$S(O)_2O^-$ such as benzenesulfonate and toluenesulfonate or tosylate; v) citrate; vi) succinate; vii) tartrate; viii) lactate; ix) alkyl sulfates: Alk-O—$S(O)O^-$ such as methyl sulfate and ethyl sulfate; x) aryl sulfates: Ar—O—$S(O)O^-$ such as benzene sulfate and toluene sulfate; xi) alkoxy sulfates: Alk-O—$S(O)_2O^-$ such as methoxy sulfate and ethoxy sulfate; xii) aryloxy sulfates: Ar—O—$S(O)_2O^-$, xiii) phosphates $O{=}P(OH)_2{-}O^-$, $O{=}P(O^-)_2{-}OH$ $O{=}P(O^-)_3$, HO-$[P(O)(O^-)]_w{-}P(O)(O^-)_2$ with w being an integer; xiv) acetate; xv) triflate; and xvi) borates such as tetrafluoroborate, xvii) disulfate $(O{=})_2S(O^-)_2$ or $SO_4^{2-}$ and monosulfate $HSO_4^-$.

the anionic counterion, derived from the organic or mineral acid salt, ensures the electrical neutrality of the molecule; thus, it is understood that when the anion comprises several anionic charges, then the same anion may serve for the electrical neutrality of several cationic groups in the same molecule or else may serve for the electrical neutrality of several molecules; for example, a dye of formula (I) which contains two cationic chromophores may contain either two "singly charged" anionic counterions or a "doubly charged" anionic counterion such as $(O{=})_2S(O^-)_2$ or $O{=}P(O)_2{-}OH$.

In the context of the invention, the term "derivative of formula (I)" is intended to mean all mesomeric, tautomeric or optical or geometrical isomer forms.

The term "addition salts" is intended to mean the salts of physiologically acceptable organic or mineral acids of the compounds of formula (I).

The compounds of formula (I) may optionally be salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

Moreover, the addition salts that may be used in the context of the invention are also chosen from addition salts with a cosmetically acceptable base such as the basifying agents as defined below, for instance alkali metal hydroxides such as sodium hydroxide, potassium hydroxide, aqueous ammonia, amines or alkanolamines.

The compounds of formula (I) may also be in the form of solvates, for example a hydrate or a solvate of a linear or branched alcohol such as ethanol or isopropanol.

According to one particular embodiment of the invention, the compounds of formula (I) are cationic.

According to another particular embodiment of the invention, the compounds of formula (I) are non-cationic.

According to one preferred embodiment, in formula (I), $R_1$ and $R_2$ represent a hydrogen atom.

According to one advantageous embodiment of the invention, when the compound of formula (I) is such that K represents a radical of formula (II), $R_4$ represents a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$ and $C_1$-$C_6$ alkylpiperidinium An$^-$. More preferentially, $R_4$ denotes a linear or branched $C_1$-$C_6$, preferentially $C_1$-$C_4$, alkyl radical which is optionally substituted with one or more hydroxyl radicals, in particular unsubstituted, and more preferably $R_4$ denotes a methyl radical.

According to one particular embodiment of the invention, when the compound of formula (I) is such that K represents a radical of formula (II), X denotes, according to a first preferred embodiment, a radical —$NR_{11}R_{12}$.

According to a first variant, X denotes a radical $NR_{11}R_{12}$ wherein $R_{11}$ and $R_{12}$ denote:
a hydrogen atom
a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, linear or branched $C_1$-$C_6$ alkyl, $C_1$-$C_6$ alkylimidazole, and $C_1$-$C_6$ alkylimidazolium An$^-$, preferably substituted with one or more radicals, which may be identical or different, chosen from hydroxyl and $C_1$-$C_6$ alkylimidazolium An$^-$.

Preferably, $R_{11}$ and $R_{12}$ independently represent a hydrogen atom, a hydroxyethyl radical, an ethyl radical, an isopropyl radical, and a propylimidazolium, An⁻ radical, substituted with a methyl radical.

According to a second variant, X denotes a radical —$NR_{11}R_{12}$ wherein $R_{11}$ and $R_{12}$ form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals, which may be identical or different, chosen from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium or linear or branched $C_1$-$C_6$ alkyl.

Preferably, X denotes a radical —$NR_{11}R_{12}$ wherein $R_{11}$ and $R_{12}$ form, together with the nitrogen to which they are attached, a cationic or non-cationic, 5- or 6-membered, non-aromatic heterocycle which may contain one or more nitrogen atoms and which may itself be substituted with one or more radicals, which may be identical or different, chosen from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium or linear or branched $C_1$-$C_6$ alkyl. More preferentially, X denotes a radical —$NR_{11}R_{12}$ wherein $R_{11}$ and $R_{12}$ form, together with the nitrogen atom to which they are attached, a cationic or non-cationic, preferably cationic, 5- or 6-membered, preferably 5-membered, non-aromatic heterocycle which may contain one or two nitrogen atoms and which may itself be substituted with one or more radicals, which may be identical or different, chosen from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, or linear or branched $C_1$-$C_6$ alkyl, preferably $C_1$-$C_6$ tri(hydroxy)alkylammonium, more preferentially $C_1$-$C_6$ trialkylammonium.

According to one particular embodiment of the invention, when the compound of formula (I) is such that K represents a radical of formula (II), X denotes, according to a second preferred embodiment, a hydroxyl radical.

According to one embodiment of the invention, in formula (I), when K represents a radical of formula (IV), R'4 preferably denotes:

a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, preferably optionally substituted with one or more different radicals chosen from hydroxyls, amino, and $C_1$-$C_6$ mono(hydroxy)alkylamino or di(hydroxy)alkylamino;

a linear or branched $C_1$-$C_6$ alkoxy radical which may be substituted with one or more radicals, which may be identical or different, chosen from hydroxyls, amino, $C_1$-$C_6$ mono(hydroxy)alkylamino or di(hydroxy)alkylamino, preferably optionally substituted with one or more different radicals chosen from hydroxyls, amino, and $C_1$-$C_6$ mono(hydroxy)alkylamino or di(hydroxy)alkylamino;

a halide.

According to one particular embodiment, in formula (I), when K represents a radical of formula (III), $R_5$ advantageously represents a radical —$NR_7R_8$.

According to one variant, $R_5$ represents a radical —$NR_7R_8$ wherein $R_7$ and $R_8$ independently denote:

a hydrogen atom;

a linear or branched $C_1$-$C_6$ alkyl radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, and $C_1$-$C_6$ alkylpiperidinium An⁻; and preferably wherein $R_7$ and $R_8$ independently denote:

a hydrogen atom, a linear or branched $C_1$-$C_6$ alkyl radical which may be substituted with one or more radicals, which may be identical or different, chosen from hydroxyls, amino, and $C_1$-$C_6$ mono(hydroxy)alkylamino or di(hydroxy)alkylamino.

According to one preferred variant, $R_5$ represents a radical —$NR_7R_8$ wherein $R_7$ and $R_8$ denote a hydrogen atom.

According to one embodiment, when the compound of formula (I) is such that K represents a radical of formula (III), $R_6$ advantageously represents a radical —$NR_9R_{10}$.

Preferably, $R_9$ and $R_{10}$ form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals, which may be identical or different, chosen from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium or linear or branched $C_1$-$C_6$ alkyl.

More preferentially, $R_9$ and $R_{10}$ form, together with the nitrogen to which they are attached, a piperazinium ring substituted with one or more linear or branched $C_1$-$C_6$ alkyl radicals and even more preferentially an N-dimethylpiperazinium ring.

According to another embodiment, when the compound of formula (I) is such that K represents a radical of formula (III), $R_6$ advantageously represents a linear or branched $C_1$-$C_6$ alkoxy radical which may be substituted with one or more radicals, which may be identical or different, chosen from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, and $C_1$-$C_6$ alkylpiperidinium An⁻. Preferably, $R_6$ represents a linear or branched $C_1$-$C_6$ alkoxy radical which may be substituted with one or more radicals, which may be identical or different, chosen from hydroxyls, amino, and $C_1$-$C_6$ mono(hydroxy)alkylamino or di(hydroxy)alkylamino. More preferentially, $R_6$ represents a linear or branched $C_1$-$C_6$ alkoxy radical which may be substituted with a radical chosen from hydroxyl, amino, and $C_1$-$C_6$ mono(hydroxy)alkylamino or di(hydroxy)alkylamino, such as the radical —O—$(CH_2)_2$—OH.

As examples of dyes of formula (I), mention may be made of the compounds presented below:

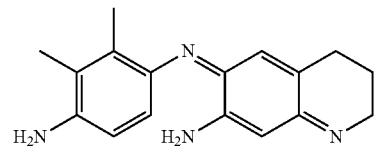

6-[(Z)-4-Amino-2,3-dimethylphenylimino]-2,3,4,6-tetrahydroquinolin-7-ylamine

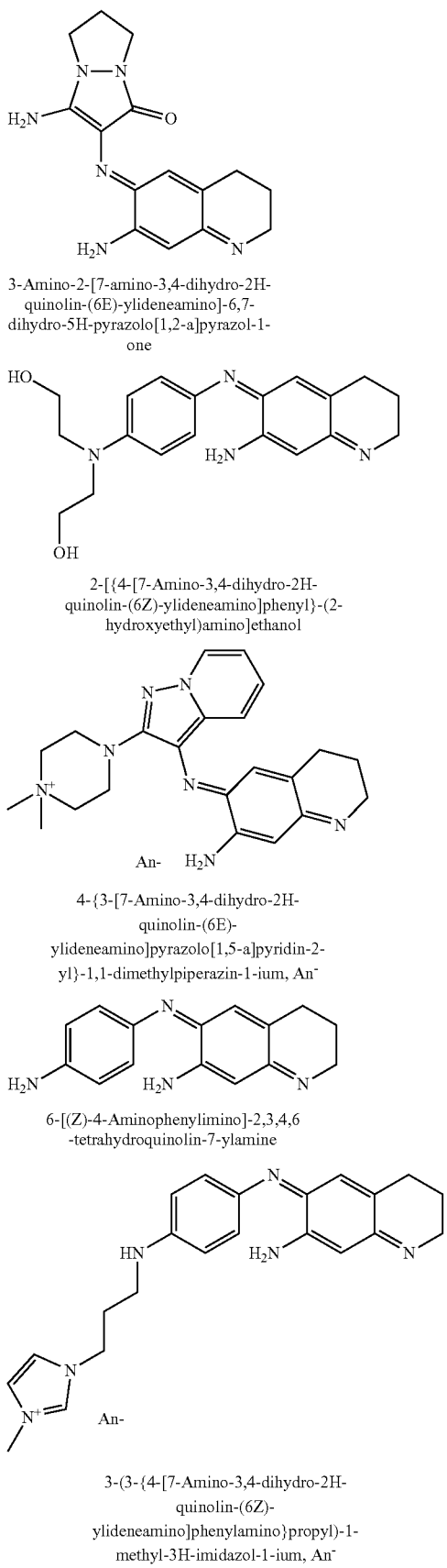
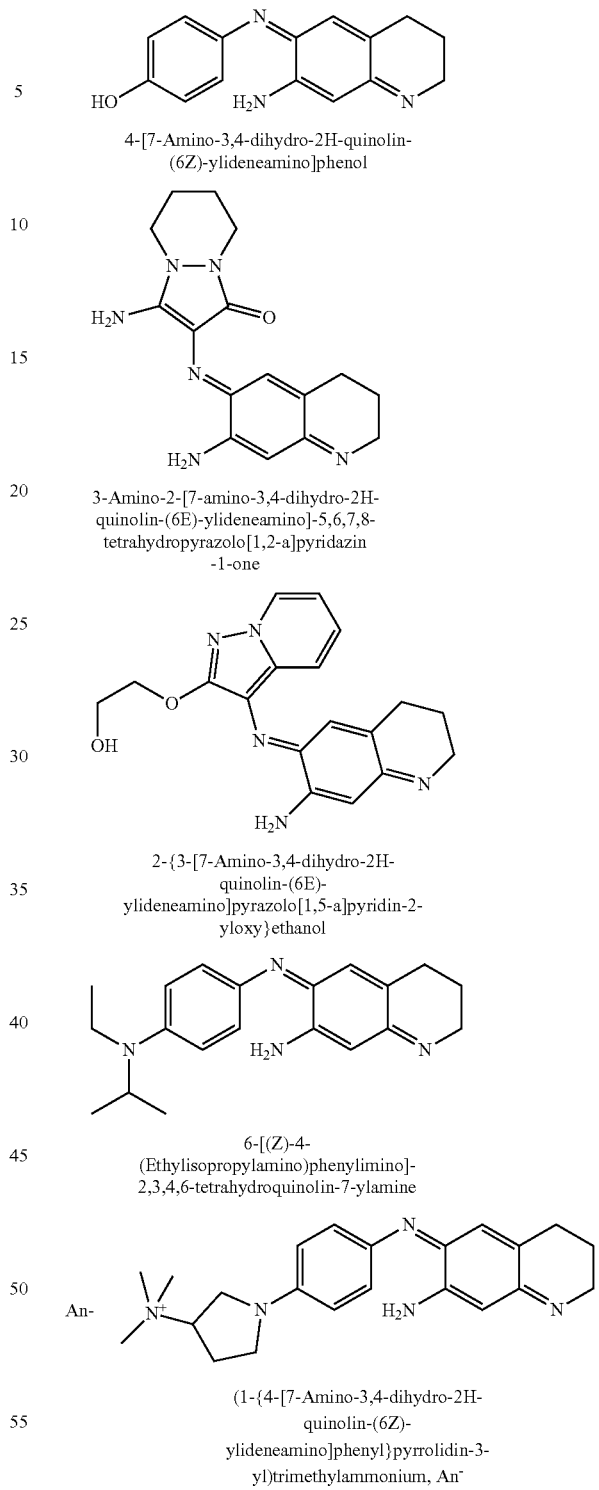
and also the optical isomers, geometrical isomers, tautomers, solvates and addition salts thereof.
The compounds (I) of the invention can be synthesized by reacting the compounds of formula A below with the compounds (II'), (III') or (IV') below in the presence of an oxidizing agent, the oxidizing agent possibly being air or aqueous hydrogen peroxide:

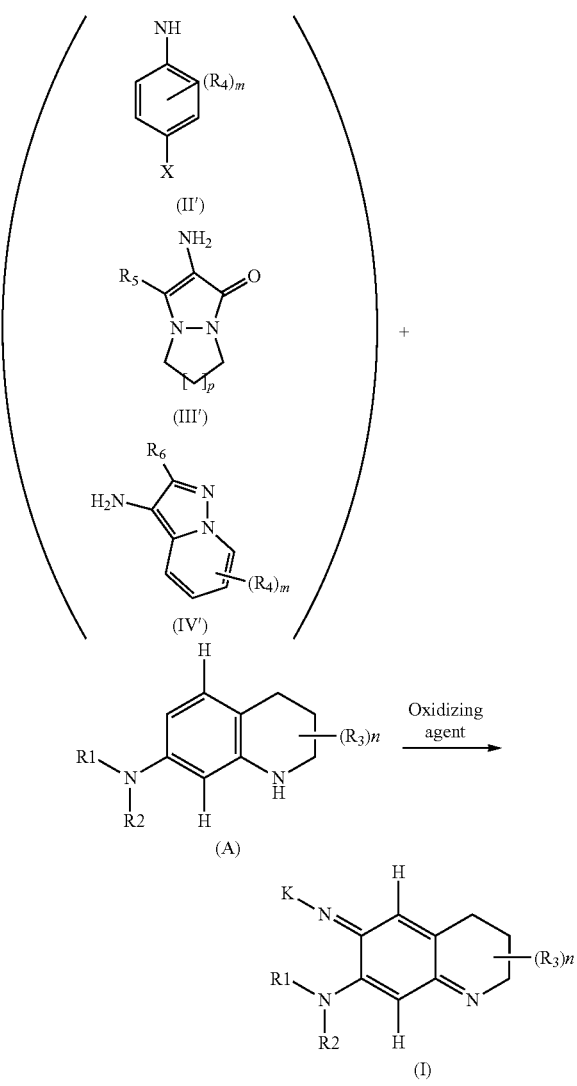

This reactivity principle is in particular described in the literature references attached hereto: FR3006182, FR3006181, WO2013087768, FR2983710.

A subject of the present invention is also a composition for dyeing keratin fibers, comprising, in a medium that is suitable in particular for dyeing keratin fibers such as the hair, at least one compound of formula (I) as defined previously, and also the optical isomers, geometrical isomers and tautomers thereof, and also the addition salts thereof with an acid or a base, and the solvates thereof such as hydrates.

According to a particular embodiment of the invention, the compound(s) of formula (I) as defined previously represent from 0.01% to 15% and more particularly from 0.05% to 10% by weight relative to the total weight of the composition.

The dye composition that is useful in the context of the invention may furthermore comprise an oxidation base. This oxidation base may be chosen from the oxidation bases conventionally used in oxidation dyeing, for example para-phenylenediamines, bis(phenyl)alkylenediamines, para-aminophenols, ortho-aminophenols and heterocyclic bases.

Among the para-phenylenediamines, examples that may be mentioned more particularly include para-phenylenediamine, para-tolylenediamine, 2-chloro-para-phenylenediamine, 2,3-dimethyl-p ara-phenylenediamine, 2,6-dimethyl-para-phenylenediamine, 2,6-diethyl-para-phenylenediamine, 2,5-dimethyl-p ara-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetyl amino ethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene, 2-(2,5-diaminophenyl)ethanol, 2-(methoxymethyl)benzene-1,4-diamine, 3(-2,5-diaminophenyl)prop an-1-ol and 1-{3-[(4-aminophenyl)amino]propyl}-3-methyl-1H-imidazol-3-ium chloride, and the acid addition salts thereof.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-p ara-phenylenediamine, 2-(2,5-diaminophenyl)ethanol, 2-(methoxymethyl)benzene-1,4-diamine, 3(-2,5-diaminophenyl)propan-1-ol and 1-{3-[(4-aminophenyl)amino]propyl}-3-methyl-1H-imidazol-3-ium chloride, and the addition salts thereof with an acid, are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetra-methylenediamine, N,N'-bis((3-hydroxyethyl)-N,N'-bis(4-aminophenyl)tetramethylenediamine, N,N'-bis(4-methylaminophenyl)tetra-methylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid.

Among the para-aminophenols that may be mentioned, for example, are para-aminophenol, 4-amino-3-methylphenol, 4-amino-3-fluorophenol, 4-amino -3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the acid addition salts thereof.

The ortho-aminophenols include, for example, 2-aminophenol, 2-amino-5-methylphenol, 2-amino-6-methylphenol, 5-acetamido-2-aminophenol, and their addition salts with an acid.

Among the heterocyclic bases, examples that may be mentioned include pyridine derivatives, pyrimidine derivatives and pyrazole derivatives, and derivatives of pyrazolo[1,2-a]pyrazol- 1-one type and derivatives of pyrazolopyridine type as described in European patent applications Nos 1 792 903 and 1 792 606.

Among the pyridine derivatives, mention may be made of the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid addition salts thereof.

Among the pyrimidine derivatives, mention may be made of the compounds described, for example, in patents DE 2 359 399; JP 88-169 571; JP 05 163 124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048, and among which mention may be made of pyrazolo[1,5-a]pyrimidine-3,7-diamine, 2,5-dimethylpyrazo lo [1,5-a] pyrimidine-3 ,7-diamine, pyrazolo [1,5-a]pyrimidine-3,5-diamine, 2,7-dimethylpyrazolo [1,5-a]pyrimidine-3,5-diamine, 3-aminopyrazolo [1,5-a]pyrimidin-7-ol, 3-aminopyrazolo [1,5-a]pyrimidin-5-ol, 2-(3-aminopyrazolo [1,5-a]pyrimidin-7-ylamino)ethanol, 2-(7-aminopyrazolo[1,5-a]pyrimidin-3-ylamino)ethanol, 2-[(3-aminopyrazolo [1,5-a]pyrimidin-7-yl)(2-hydroxyethyl)amino]ethanol, 2-[(7-aminopyrazolo [1,5-a]pyrimidin-3-yl)(2-hydroxyethyl)amino]ethanol, 5,6-dimethylpyrazolo [1,5-a]pyrimidine-3,7-diamine, 2,6-dimethylpyrazolo [1,5-a]pyrimidine-3,7-diamine, 2,5,N7,N7-tetramethylpyrazolo [1,5-a]pyrimidine-3,7-diamine and 3-amino-5-methyl-7-imidazolylpropylaminopyrazolo[1,5-a]pyrimidine, and the acid addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole , 1-benzyl-4,5-diamino -3-methylpyrazole, 4,5-diamino-3-tert-butyl-1-methylpyrazole , 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-amino ethyl) amino-1,3-dimethylpyrazole, 3 ,4,5-triaminopyrazole, 1-methyl-3 ,4,5-tri aminopyrazole, 3,5-diamino-1-methyl-4-methylaminopyrazole and 3,5-diamino-4-(β-hydroxyethyl) amino-1-methylpyrazole, and the acid addition salts thereof.

Among the derivatives of pyrazolo[1,2a]pyrazol- 1-one type, mention may be made of compounds such as 2,3-diamino-6,7-dihydro,1H-5H-pyrazolo[1,2a]pyrazol-1-one.

The dye composition that is useful in the context of the invention may also contain one or more couplers that are conventionally used for dyeing keratin fibers. Among these couplers, mention may be made in particular of meta-phenylenediamines, meta-aminophenols, meta-diphenols, naphthalene-based couplers and heterocyclic couplers.

Examples that may be mentioned include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine 3,5-diamino-2,6-dimethoxypyridine, 1-N-(β-hydroxyethyl)amino-3,4-methylenedioxybenzene and 2,6-bis(β-hydroxyethylamino)toluene, and the acid addition salts thereof.

In general, the acid addition salts that may be used in the context of the invention for the oxidation bases and the couplers are in particular chosen from the hydrochlorides, hydrobromides, sulfates, citrates, succinates, tartrates, lactates, tosylates, benzenesulfonates, phosphates and acetates.

If the oxidation base(s) are present in the dye composition according to the invention, their amount preferably ranges from 0.001% to 10% by weight and more preferentially from 0.005% to 6% by weight relative to the total weight of the composition.

If they are present, the coupler(s) are generally present in an amount ranging from 0.001% to 10% by weight and even more preferentially from 0.005% to 6% by weight relative to the total weight of the composition.

The dye composition that is useful in the context of the invention may optionally comprise at least one additional direct dye conventionally used for the dyeing of keratin fibers. It may be chosen from cationic and nonionic species.

Non-limiting examples that may be mentioned include nitrobenzene dyes, azo, azomethine, methine, tetraazapentamethine, anthraquinone, naphthoquinone, benzoquinone, phenothiazine, indigoid, xanthene, phenanthridine and phthalocyanin dyes, triarylmethane-based dyes and natural dyes, alone or as mixtures.

It may be chosen, for example, from the following red or orange nitrobenzene dyes: 1-hydroxy-3-nitro-4-N-(γ-hydroxypropyl)aminobenzene, N-(β-hydroxyethyl)amino-3-nitro-4-aminobenzene, 1-amino-3-methyl-4-N-(β-hydroxyethyl)amino-6-nitrobenzene, 1-hydroxy-3-nitro-4-N-(β-hydroxyethyl)aminobenzene, 1,4-diamino-2-nitrobenzene, 1-amino-2-nitro-4-methylaminobenzene, N-(β-hydroxyethyl)-2-nitro-para-phenylenediamine, 1-amino-2-nitro-4-(β-hydroxyethyl)amino-5-chlorobenzene, 2-nitro-4-amino diphenyl amine, 1-amino-3-nitro-6-hydroxybenzene, 1-(β-amino ethyl)amino-2-nitro-4-(β-hydroxyethyloxy)benzene, 1-(β,γ-dihydroxypropyl)oxy-3-nitro-4-(β-hydroxyethyl) aminobenzene, 1-hydroxy-3-nitro-4-aminobenzene, 1-hydroxy-2-amino-4,6-dinitrobenzene, 1-methoxy-3-nitro-4-(β-hydroxyethyl)aminobenzene, 2-nitro-4'-hydroxydiphenylamine and 1-amino-2-nitro-4-hydroxy-5-methylbenzene.

The additional direct dye may also be chosen from yellow and green-yellow nitrobenzene direct dyes. Examples that may be mentioned include the compounds chosen from: 1-β-hydroxyethyloxy-3-methylamino-4-nitrobenzene, 1-methylamino-2-nitro-5-(β,γ-dihydroxypropyl)oxybenzene, 1-(β-hydroxyethyl)amino-2-methoxy-4-nitrobenzene, 1-(β-amino ethyl)amino-2-nitro-5-methoxybenzene, 1 ,3-bis (β-hydroxyethyl)amino-4-nitro-6-chlorobenzene, 1-amino-2-nitro-6-methylbenzene, 1-(β-hydroxyethyl)amino-2-hydroxy-4-nitrobenzene, N-(β-hydroxyethyl)-2-nitro-4-trifluoromethylaniline, 4-(β-hydroxyethyl)amino-3-nitrobenzenesulfonic acid, 4-ethylamino-3-nitrobenzoic acid, 4-(β-hydroxyethyl)amino-3-nitrochlorobenzene, 4-(β-hydroxyethyl)amino-3-nitromethylbenzene, 4-(β,γ-dihydroxypropyl)amino-3-nitrotrifluoromethylbenzene, 1-(β-ureido ethyl)amino-4-nitrobenzene, 1,3-diamino-4-nitrobenzene, 1-hydroxy-2-amino-5-nitrobenzene, 1-amino-2-[tris(hydroxymethyl)methyl]amino-5-nitrobenzene, 1-(β-hydroxyethyl)amino-2-nitrobenzene and 4-(β-hydroxyethyl)amino-3-nitrobenzamide.

Mention may also be made of blue or violet nitrobenzene direct dyes, for instance 1-(β-hydroxyethyl)amino-4-N,N-bis(β-hydroxyethyl)amino-2-nitrobenzene, 1-(γ-hydroxypropyl)amino-4-N,N-bis(β-hydroxyethyl)amino-2-nitrobenzene, 1-(β-hydroxyethyl)amino-4-(N-methyl-N-β-hydroxyethyl)amino-2-nitrobenzene, 1-(β-hydroxyethyl)amino-4-(N-ethyl-N-β-hydroxyethyl)amino-2-nitrobenzene, 1-(β,γ-dihydroxypropyl)amino-4-(N-ethyl-N-β-hydroxyethyl)amino-2-nitrobenzene, and the 2-nitro-para-phenylenediamines of formula (III) below:

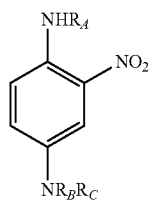

(III)

wherein:
  $R_B$ represents a $C_1$-$C_4$ alkyl radical or a β-hydroxyethyl, β-hydroxypropyl or γ-hydroxypropyl radical;
  $R_A$ and $R_C$, which may be identical or different, represent a β-hydroxyethyl, β-hydroxypropyl, γ-hydroxypropyl or β,γ-dihydroxypropyl radical, at least one of the radicals $R_B$, $R_C$ or $R_A$ representing a γ-hydroxypropyl radical and $R_B$ and $R_C$ not being able simultaneously to denote a β-hydroxyethyl radical when $R_B$ is a γ-hydroxypropyl radical, such as those described in French patent FR 2 692 572.

Among the azo direct dyes that can be used according to the invention, mention may be made of the cationic azo dyes described in patent applications WO 95/15144, WO 95/01772, EP 714 954, FR 2 822 696, FR 2 825 702, FR 2 825 625, FR 2 822 698, FR 2 822 693, FR 2 822 694, FR 2 829 926, FR 2 807 650, WO 02/078 660, WO 02/100 834, WO 02/100 369 and FR 2 844 269.

Among these compounds, mention may be made most particularly of the following dyes: 1,3-dimethyl-2-[[4-(dimethylamino)phenyl]azo]-1H-imidazolium halides, 1,3-dimethyl-2-[(4-aminophenyl)azo]-1H-imidazolium halides, 1-methyl-4-[(methylphenylhydrazono)methyl]pyridinium halides or alkyl sulfates.

Among the azo direct dyes, mention may also be made of the following dyes, described in the Color Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9.

Mention may also be made of 1-(4'-aminodiphenylazo)-2-methyl-4-bis(β-hydroxyethyl)aminobenzene and 4-hydroxy-3-(2-methoxyphenyl azo)-1-naphthalenesulfonic acid.

Among the quinone direct dyes, mention may be made of the following dyes: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the following compounds: 1-N-methylmorpholiniumpropylamino-4-hydroxyanthraquinone, 1-aminopropylamino-4-methylaminoanthraquinone, 1-aminopropylaminoanthraquinone, 5-β-hydroxyethyl-1,4-diaminoanthraquinone, 2-aminoethylaminoanthraquinone, 1,4-bis(β,γ-dihydroxypropylamino)anthraquinone.

Among the azine dyes that may be mentioned are the following compounds: Basic Blue 17, Basic Red 2.

Among the triarylmethane dyes that can be used according to the invention, mention may be made of the following compounds: Basic Green 1, Acid blue 9, Basic Violet 3, Basic Violet 14, Basic Blue 7, Acid Violet 49, Basic Blue 26, Acid Blue 7.

Among the indoamine dyes that may be used according to the invention, mention may be made of the following compounds: 2 β-hydroxyethlyamino-5-[bis(β-4'-hydroxyethyl)amino]anilino-1,4-benzoquinone, 2β-hydroxyethylamino-5-(2'-methoxy-4'-amino)anilino-1,4-benzoquinone, 3-N-(2'-chloro-4'-hydroxy)phenylacetylamino-6-methoxy-1,4-benzoquinoneimine, 3-N(3'-chloro-4'-methylamino)phenylureido-6-methyl-1,4-benzoquinoneimine and 3-[4'-N-(ethylcarbamylmethyl)amino]phenylureido-6-methyl-1,4-benzoquinoneimine.

Among the dyes of tetraazapentamethine type that may be used according to the invention, mention may be made of the following compounds: 2-((E)-{(E)-[(1,3-dimethyl-1,3-dihydro-2 H-imidazol-2-ylidene)hydrazono]methyl}diazenyl)-1,3-dimethyl-1H-imidazol-3-ium chloride; 2-{(E)-[(1Z)-N-(1,3-dimethyl-1,3-dihydro-2 H-imidazol-2-ylidene)ethanehydrazonoyl]diazenyl}-1,3-dimethyl-1H-imidazol-3-ium chloride; 4-methoxy-2-((E)-{(1E)-1-[(2E)-(4-methoxy-1-methylpyridin-2(1H)-ylidene)hydrazono]ethyl}diazenyl)-1-methylpyridinium chloride; 1-methyl-2-((E)-{(1E)-1-[(2E)-(1-methylpyridin-2(1H)-ylidene)hydrazono]ethyl}diazenyl)pyridinium chloride; 1-(2-hydroxyethyl)-2-[(E)-((1E)-1-{(2E)-[1-(2-hydroxyethyl)pyridin-2(1H)-ylidene]hydrazono}ethyl)diazenyl]pyridinium chloride; 1-methyl-2-((E)-{(E)-[(2Z)-(1-methylpyridin-2(1H)-ylidene)hydrazono]methyl}diazenyl) pyridinium chloride; 1-(2-hydroxyethyl)-2-[(E)-((E)-{(2E)-[1-(2-hydroxyethyl)pyridin-2(1H)-ylidene] hydrazono}methyl)diazenyl]pyridinium acetate.

Among the additional natural direct dyes that may be used according to the invention, mention may be made of lawsone, juglone, alizarin, purpurin, carminic acid, kermesic acid, purpurogallin, protocatechaldehyde, indigo, isatin, curcumin, spinulosin and apigenidin. Use may also be made of extracts or decoctions comprising these natural dyes and in particular henna-based poultices or extracts.

When they are present, the content of additional direct dyes in the composition generally ranges from 0.001% to 20% and preferably from 0.01% to 10% by weight relative to the weight of the composition.

The medium that is suitable for dyeing, also known as the dye support, generally comprises water or a mixture of water and of at least one organic solvent to dissolve the compounds that would not be sufficiently water-soluble.

More particularly, the organic solvents are chosen from linear or branched and preferably saturated monoalcohols and diols, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycols or glycol ethers, for instance ethylene glycol monomethyl, monoethyl and monobutyl ethers, propylene glycol or ethers thereof, for instance propylene glycol, butylene glycol or dipropylene glycol monomethyl ether; and also diethylene glycol alkyl ethers, in particular of $C_1$-$C_4$, for instance diethylene glycol monoethyl ether or monobutyl ether, alone or as a mixture.

The common solvents described above, if they are present, usually represent from 1% to 40% by weight and more preferentially from 5% to 30% by weight, relative to the total weight of the composition.

The dye composition that is useful in the context of the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

These above adjuvants are generally present in an amount, for each of them, of between 0.01% and 20% by weight relative to the weight of the composition.

Needless to say, those skilled in the art will take care to select this or these optional additional compound(s) such that the advantageous properties intrinsically associated with the dye composition that is useful in the context of the invention are not, or are not substantially, adversely affected by the envisaged addition(s).

The pH of the dye composition that is useful in the context of the invention is generally between 3 and 12 approximately and preferably between 5 and 11 approximately. It can be adjusted to the desired value by means of acidifying or basifying agents regularly used in the dyeing of keratin fibers or alternatively using conventional buffer systems. Modifying the pH within these ranges will promote the formation of the compounds (I).

Among the acidifying agents, examples that may be mentioned include mineral acids, for instance hydrochloric acid, nitric acid or sulfuric acid, or organic acids, for instance compounds comprising at least one carboxylic acid function such as acetic acid, tartaric acid, citric acid or lactic acid, a sulfonic acid function, a phosphonic acid function or a phosphoric acid function.

Among the basifying agents, examples that may be mentioned include aqueous ammonia, alkali metal carbonates, alkanolamines such as monoethanolamine, diethanolamine and triethanolamine, and also derivatives thereof, sodium hydroxide, potassium hydroxide and the compounds of formula (IV) below:

$$\begin{array}{c} R_a \\ \diagdown \\ R_c \end{array} NW - N \begin{array}{c} R_b \\ \diagup \\ R_d \end{array} \quad (IV)$$

wherein W is a propylene residue optionally substituted with a hydroxyl group or a $C_1$-$C_4$ alkyl radical; and Ra, Rb, Rc and Rd, which may be identical or different, represent a hydrogen atom or a $C_1$-$C_4$ alkyl or $C_1$-$C_4$ hydroxyalkyl radical.

The oxidizing agent will also be necessary for obtaining simultaneous lightening of the keratin fibers (lightening dyeing) and/or when the composition contains oxidation bases or couplers.

The composition according to the invention may also contain one or more oxidizing agents.

The oxidizing agent may be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. The oxidizing agent will preferably be hydrogen peroxide.

In the case where the oxidizing agent(s) are present in the dye composition according to the invention, their amount will preferably range from 5% to 100% by weight and better still from 50% to 100% by weight relative to the total weight of the composition.

The dye composition that is useful in the context of the invention may be in various forms, such as in the form of liquids, creams or gels, or in any other form that is suitable for dyeing keratin fibers, and in particular human hair.

A subject of the present invention is also the use of the compounds of formula (I) as defined previously, and also the optical isomers, geometrical isomers and tautomers thereof, and the addition salts thereof with an acid or a base and the solvates thereof, for dyeing keratin fibers, in particular human keratin fibers such as the hair.

The dyeing process of the invention comprises the application to the keratin fibers of at least one dye composition as defined above.

When an oxidizing agent is used, it may be present in the composition of the invention. It may also be applied separately, as a pretreatment or post-treatment.

The application of the composition of the invention may optionally be followed by rinsing.

The leave-on time for the dye composition is generally between 3 and 60 minutes, preferably between 5 and 40 minutes and even more preferentially between 10 and 30 minutes.

The application temperature generally used is ambient temperature, preferably between 25 and 55° C.

A subject of the present invention is also a multi-compartment device or kit for performing the process for dyeing keratin fibers, described above.

The examples that follow serve to illustrate the invention without, however, being limiting in nature.

EXAMPLES

Example 1

Synthesis of 6-[(Z)-4-Amino-2,3-dimethylphenylimino]-2,3,4,6-tetrahydroquinolin-7-ylamine hydrochloride (1)

Compound 1

(a) 2,3-dimethylbenzene-1,4-diamine ·2HCl + (b) 1,2,3,4-tetrahydroquinolin-7-amine ·2HCl →

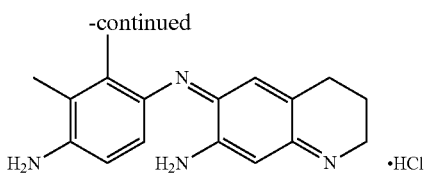

In a 500 ml round-bottomed flask, 9.91 g of 2,3-dimethylbenzene-1,4-diamine dihydrochloride (commercial) (a) and 10.48 g of 1,2,3,4-tetrahydroquinolin-7-ylamine dihydrochloride (commercial) (b) are added to 250 ml of water and the pH is adjusted to 9.5 with 20% aqueous ammonia. After 72 hours of stirring, the gum formed is purified by silica column chromatography.

2.98 g of product are recovered with a purity of 92%. After washing of the powder with acetonitrile, 2.35 g of 6-[(Z)-4-amino-2,3-dimethylphenylimino]-2,3,4,6-tetrahydroquinolin-7-ylamine (1) are obtained with a purity of 95%.

The NMR and mass analyses are in accordance with the expected structure (1).

Example 2

Synthesis of 4-{3-[7-Amino-3,4-dihydro-2H-quinolin-(6E)-ylideneamino]pyrazolo[1,5-a]pyridin-2-yl}-1,1-dimethylpiperazin-1-ium chloride (2)

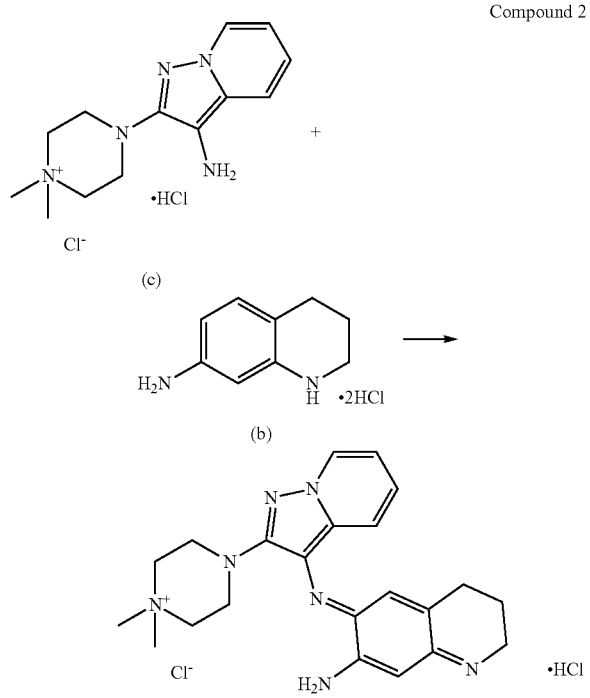

0.722 g of 4-(3-aminopyrazolo[1,5-a]pyridin-2-yl)-1,1-dimethylpiperazin-1-ium chloride hydrochloride (described in FR3022454) (c) and 0.502 g of 1,2,3,4-tetrahydroquinolin-7-ylamine dihydrochloride (commercial) (b) are added to 15 ml of water and then the pH is adjusted to 9.5 with 20% aqueous ammonia. After 24 hours of stirring, 100 ml of isopropanol are added and the reaction medium is evaporated to dryness. 20 ml of methanol are added to the resulting powder and, after the insoluble material (ammonium chloride) has been filtered off, the filtrate is concentrated 788 mg of compound (2) are thus obtained in the form of a blue-black powder.

The NMR and mass analyses are in accordance with the expected structure (2).

Example 3

Synthesis of 3-Amino-2-[7-amino-3,4-dihydro-2H-quinolin-(6E)-ylideneamino]-6,7-dihydro-5H-pyrazolo[1,2-a]pyrazol-1-one chloride (3)

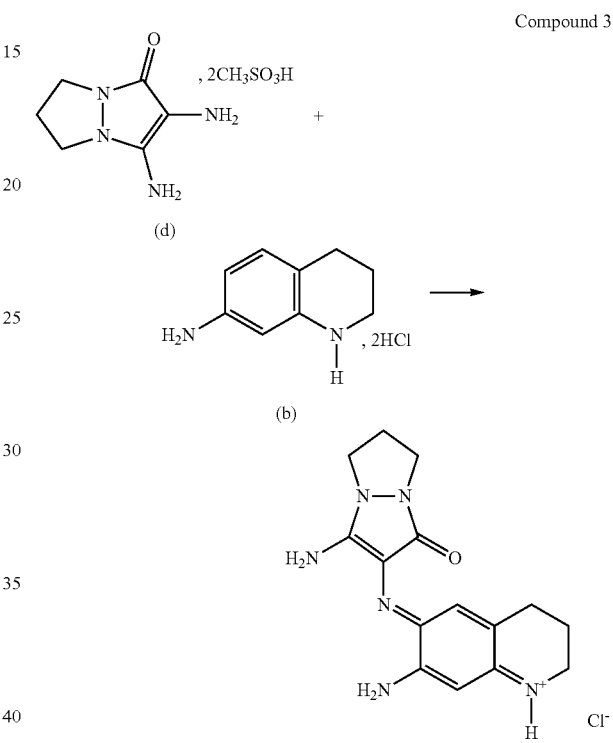

0.288 mmol of 2,3-diamino-6,7-dihydro-1H,5H-pyrazolo[1,2-a]pyrazol-1-one dimethanesulfonate (100 mg, 1 equivalent) (commercial) (d) and 0.288 mmol of 1,2,3,4-tetrahydroquinolin-7-amine dihydrochloride (63.8 mg, 1 equivalent) (commercial) (b) are introduced into a 25 ml round-bottomed flask containing 5 ml of water, 1 ml of 20% aqueous ammonia and 0.5 ml of 6% aqueous hydrogen peroxide. The reaction medium is stirred at ambient temperature for 2 hours and then concentrated in a rotary evaporator so as to give 170 mg of a black solid.

Normal-phase chromatography of the black solid on silica, carried out with an eluent constituted of dichloromethane and methanol, makes it possible to obtain 14.5 mg of (6E)-7-amino-6-[(3-amino-1-oxo-6,7-dihydro-1H,5H-pyrazolo[1,2-a]pyrazol-2-yl)imino]-2,3,4,6-tetrahydroquinolinium chloride (3) in the form of a black powder with a yield of 16%.

The NMR and mass analyses are in accordance with the expected structure (3).

Example 4

Dyeing Compositions

The following dye compositions are prepared from the ingredients indicated in the table below:

|  | Composition 1 | Composition 2 |
|---|---|---|
| Compound 1 (according to example 1) | 500 mg |  |
| Compound 2 (according to example 2) |  | 500 mg |
| water | 80 g | 80 g |
| ethanol | 15 g | 15 g |
| Benzyl alcohol | 5 g | 5 g |

1.25 g of each composition 1 and 2 are applied to a lock of 0.25 g of gray hair containing 90% white hairs. After a leave-on time of 30 minutes at ambient temperature, the lock is rinsed, washed with a standard shampoo and then dried.

The colors of the locks thus obtained were evaluated in the CIE L*a*b* system, by means of a Minolta CM-3610d colorimeter, the values being exploited with the Spectra Magix NX software.

In this L*a*b* system, the three parameters denote, respectively, L*: the color intensity, a*: the green/red color axis, and b*: the blue/yellow color axis. For the intensity, the lower the value, the darker and more intense the color.

The variation in coloring or gain in color build-up is the difference in color between the locks of hair treated with the composition according to the invention, and the untreated locks, and is measured by (ΔE) according to the following equation:

$$\Delta E = \sqrt{(L^* - L_o^*)^2 + (a^* - a_o^*)^2 + (b^* - b_o^*)^2}$$

In this equation, L*, a* and b* represent the values measured on NG dyed hair according to the invention, and $L_o^*$, $a_o^*$ and $b_o^*$ represent the values measured on the untreated locks.

The higher the value of ΔE, the greater the gain in color build-up.

The results are indicated in the table below.

|  | Composition 1 | Composition 2 |
|---|---|---|
| Color of the locks (colorimetric data) | Blue<br>L = 18.87<br>a = −1.13<br>b = −8.90<br>ΔE = 46.96 | Blue-green<br>L = 24.35<br>a = −5.75<br>b = −13.02<br>ΔE = 47.89 |

The invention claimed is:

1. A compound of formula (I) below, an optical isomer thereof, a geometrical isomer thereof, a tautomer thereof, a salt thereof with an acid or a base, or a solvate thereof:

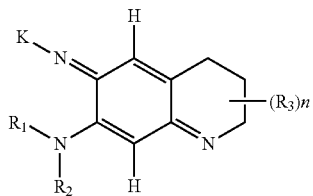

(I)

wherein:
n represents an integer equal to 0, wherein positions not substituted with a radical $R_3$ carry a hydrogen atom,
$R_1$ and $R_2$ represent
a hydrogen atom,
$R_3$ represents:
a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
K represents a radical corresponding to general formulae (II) to (IV) below:

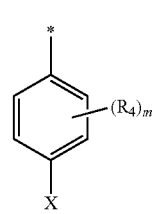

(II)

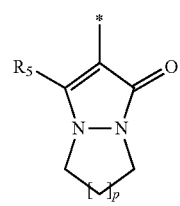

(III)

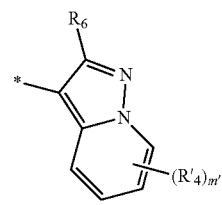

(IV)

wherein:
m represents an integer equal to 0, 1, 2, 3 or 4, wherein positions not substituted with a radical $R_4$ carry a hydrogen atom,
m' represents an integer equal to 0, 1, 2, 3 or 4, wherein positions not substituted with a radical $R'_4$ carry a hydrogen atom,
p represents an integer equal to 0, 1, 2, 3 or 4,
$R_4$ represents:
a linear or branched $C_1$-$C_6$ alkyl radical optionally substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
a linear or branched $C_1$-$C_6$ alkoxy radical optionally substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
a halide,
$R'_4$ represents:
a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;

a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;

a halide, $R_5$ represents:
- a hydrogen atom,
- a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
- a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻,
- a halide,
- a hydroxyl radical,
- a radical —$NR_7R_8$,
  wherein $R_7$ and $R_8$ independently represent
    - a hydrogen atom,
    - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
    - $R_7$ and $R_8$ may form, together with the nitrogen to which they are attached, a cationic or non-cationic, 4- to 7-membered, heterocycle which may contain one or more nitrogen, oxygen or sulfur atoms and which may itself be substituted with one or more radicals, which may be identical or different, selected from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium or linear or branched $C_1$-$C_6$ alkyl, $R_6$ represents:
- a hydrogen atom,
- a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻,
- a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻,
- a halide,
- a hydroxyl radical,
- a radical —$NR_9R_{10}$,
  wherein $R_9$ and $R_{10}$ independently represent
    - a hydrogen atom
    - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, $C_1$-$C_6$ alkylpiperidinium An⁻, or linear or branched $C_1$-$C_6$ alkyl
    - $R_9$ and $R_{10}$ may form, together with the nitrogen to which they are attached, a cationic or non-cationic, 4- to 7-membered. non-aromatic heterocycle which may contain one or more nitrogen, oxygen or sulfur atoms and which may itself be substituted with one or more radicals, which may be identical or different, selected from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium or linear or branched $C_1$-$C_6$ alkyl, X represents:
- a hydroxyl radical,
- a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
- a radical —$NR_{11}R_{12}$,
  wherein $R_{11}$ and $R_{12}$ independently represent
    - a hydrogen atom,
    - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, linear or branched $C_1$-$C_6$ alkyl, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻,
    - $R_{11}$ and $R_{12}$ may form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals, which may be identical or different, selected from hydroxyl, amino, $C_1$-$C_6$ mono(hydroxy)alkylamino, $C_1$-$C_6$ di(hydroxy)alkylamino $C_1$-$C_6$ alkoxy $C_1$-$C_6$ tri(hydroxy)alkylammonium, $C_1$-$C_6$ alkylimidazolium, $C_1$-$C_6$ alkylpyridinium or linear or branched $C_1$-$C_6$ alkyl, wherein when the compound of formula (I) is positively charged, then it comprises as many anionic counterion(s) An⁻ as cationic charge(s) to achieve the electrical neutrality of the molecule.

2. The compound as claimed in claim 1, wherein $R_4$ represents a linear or branched C1-C6 alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻.

3. The compound as claimed in claim 1, wherein $R_4$ represents a linear or branched $C_1$-$C_6$.

4. The compound as claimed in claim 1, wherein $R'_4$ represents:
a linear or branched $C_1$-$C_6$ alkyl radical which may be substituted with one or more radicals, which may be identical or different, selected from hydroxyls, amino, $C_1$-$C_6$ mono(hydroxy)alkylamino, or di(hydroxy)alkylamino,
a linear or branched $C_1$-$C_6$ alkoxy radical which may be substituted with one or more radicals, which may be identical or different, selected from hydroxyls, amino, $C_1$-$C_6$ mono(hydroxy)alkylamino, or di(hydroxy)alkylamino;
a halide.

5. The compound as claimed in claim 1, wherein $R_5$ represents a radical $-NR_7R_8$ wherein R7 and R8 independently denote:
a hydrogen atom,
a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, $C_1$-$C_6$ alkylpiperidinium An⁻.

6. The compound as claimed in claim 1, wherein $R_5$ represents a radical $—NR_7R_8$ wherein $R_7$ and $R_8$ denote a hydrogen atom.

7. The compound as claimed in claim 1, wherein $R_6$ represents a radical $—NR_9R_{10}$ wherein $R_9$ and $R_{10}$ form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals, which may be identical or different, selected from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium, or linear or branched $C_1$-$C_6$ alkyl.

8. The compound as claimed in claim 1, wherein $R_6$ represents a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An−, $C_1$-$C_6$ alkylpyridinium An⁻, or $C_1$-$C_6$ alkylpiperidinium An⁻.

9. The compound as claimed in claim 1, wherein X denotes a radical $—NR_{11}R_{12}$ wherein $R_{11}$ and $R_{12}$ denote:
a hydrogen atom,
a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, linear or branched $C_1$-$C_6$ alkyl, $C_1$-$C_6$ alkylimidazole, or $C_1$-$C_6$ alkylimidazolium An⁻.

10. The compound as claimed in claim 1, wherein $R_{11}$ and $R_{12}$ independently represent a hydrogen atom, a hydroxyethyl radical, an ethyl radical, an isopropyl radical, or a methyl substituted propylimidazolium An− radical.

11. The compound as claimed in claim 1, wherein X represents a radical $—NR_{11}R_{12}$ wherein $R_{11}$ and $R_{12}$ form, together with the nitrogen to which they are attached, a cationic or non-cationic. 4- to 7-memberednon-aromatic heterocycle which may contain one or more nitrogen, oxygen or sulfur atoms, and which may itself be substituted with one or more radicals, which may be identical or different, seelcted from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, alkylimidazolium, or $C_1$-$C_6$ alkylpyridinium or linear or branched $C_1$-$C_6$ alkyl.

12. The compound as claimed in claim 1, wherein X represents a radical $–NR_{11}R_{12}$ wherein $R_{11}$ and R12 form, together with the nitrogen to which they are attached, a cationic or non-cationicnon-aromatic heterocycle which may contain one or two nitrogen atoms and which may itself be substituted with one or more radicals, which may be identical or different, selected from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, or linear or branched $C_1$-$C_6$ alkyl.

13. The compound as claimed in claim 1, wherein X denotes a hydroxyl radical.

14. The compound as claimed in claim 1, wherein the compound is selected from the formulas below:

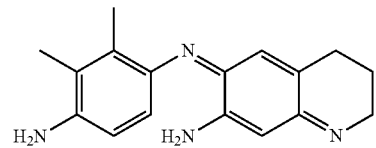

6-[(Z)-4-Amino-2,3-dimethylphenylimino]-2,3,4,6-tetrahydroquinolin-7-ylamine

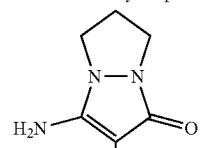

3-Amino-2-[7-amino-3,4-dihydro-2H-quinolin-(6E)-ylideneamino]-6,7-dihydro-5H-pyrazolo[1,2-a]pyrazol-1-one

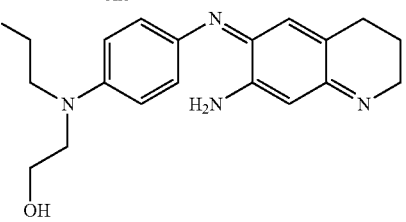

2-[{4-[7-Amino-3,4-dihydro-2H-quinolin-(6Z)-ylideneamino]phenyl}-(2-hydroxyethyl)amino]ethanol -continued

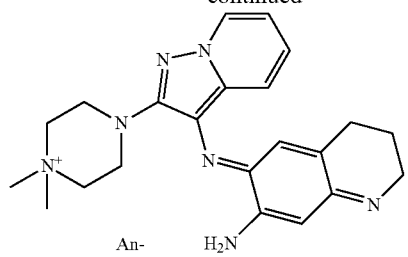

4-{3-[7-Amino-3,4-dihydro-2H-
quinolin-(6E)-
ylideneamino]pyrazolo[1,5-a]pyridin-
2-yl}-1,1-dimethylpiperazin-1-ium,
An⁻

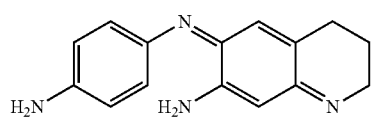

6-[(Z)-4-Aminophenylimino]-2,3,4,6
-tetrahydroquinolin-7-ylamine

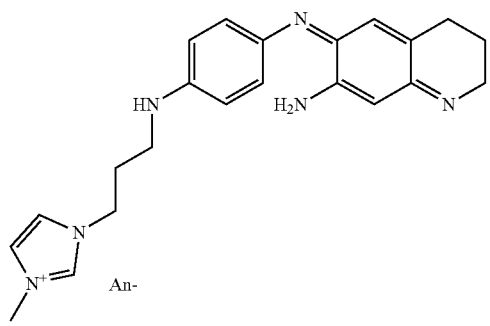

3-(3-{4-[7-Amino-3,4-dihydro-2H-
quinolin-(6Z)-
ylideneamino]phenylamino}propyl)-
1-methyl-3H-imidazol-1-ium, An⁻

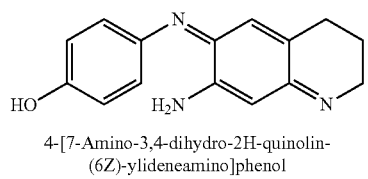

4-[7-Amino-3,4-dihydro-2H-quinolin-
(6Z)-ylideneamino]phenol

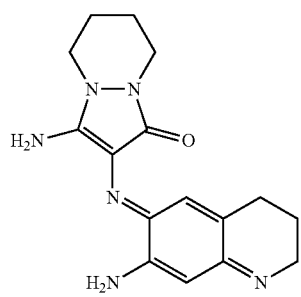

3-Amino-2-[7-amino-3,4-dihydro-2H-
quinolin-(6E)-ylideneamino]-5,6,7,8-
tetrahydropyrazolo[1,2-a]pyridazin
-1-one -continued

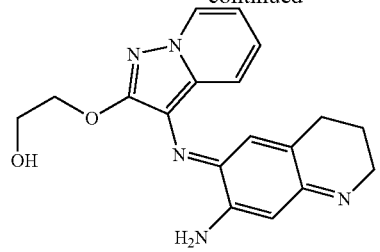

2-{3-[7-Amino-3,4-dihydro-2H-
quinolin-(6E)-
ylideneamino]pyrazolo[1,5-a]pyridin-
2-yloxy}ethanol

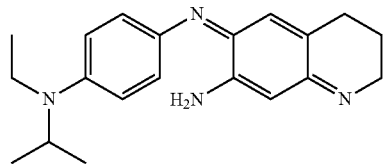

6-[(Z)-4-
(Ethylisopropylamino)phenylimino]-
2,3,4,6-tetrahydroquinolin-7-ylamine

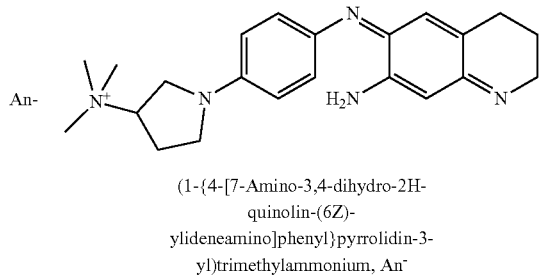

(1-{4-[7-Amino-3,4-dihydro-2H-
quinolin-(6Z)-
ylideneamino]phenyl}pyrrolidin-3-
yl)trimethylammonium, An⁻ or salts, isomers, tautomers, or solvates thereof.

15. A composition for dyeing keratin fibers comprising, in a medium that is suitable for dyeing keratin fibers, one or more compounds of formula (I) below, an optical isomer, a geometrical isomer or a tautomer thereof, a salt thereof with an acid or a base, or a solvate thereof:

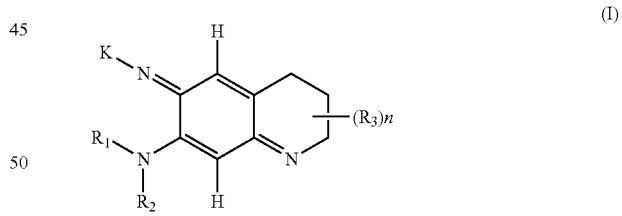

(I)

wherein:
n represents an integer equal to 0, wherein positions not substituted with a radical $R_3$ carry a hydrogen atom,
$R_1$ and $R_2$ represent
a hydrogen atom
$R_3$ represents:
a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;

K represents a radical corresponding to general formulae (II) to (IV) below:

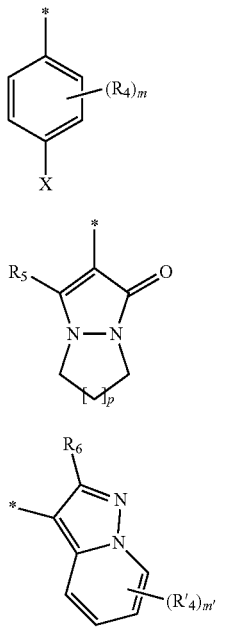

(II)

(III)

(IV)

wherein:
- m represents an integer equal to 0, 1, 2, 3 or 4, wherein positions not substituted with a radical $R_4$ carry a hydrogen atom,
- m' represents an integer equal to 0, 1, 2, 3 or 4, wherein positions not substituted with a radical $R'_4$ carry a hydrogen atom,
- p represents an integer equal to 0, 1, 2, 3 or 4,
- $R_4$ represents:
  - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, or $C_1$-$C_6$ alkylpiperidinium An$^-$;
  - a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, or $C_1$-$C_6$ alkylpiperidinium An$^-$;
  - a halide,
- $R'_4$ represents:
  - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, or $C_1$-$C_6$ alkylpiperidinium An$^-$;
  - a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, or $C_1$-$C_6$ alkylpiperidinium An$^-$;
  - a halide,
- $R_5$ represents:
  - a hydrogen atom,
  - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, or $C_1$-$C_6$ alkylpiperidinium An$^-$;
  - a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, or $C_1$-$C_6$ alkylpiperidinium An$^-$,
  - a halide,
  - a hydroxyl radical,
  - a radical —$NR_7R_8$,
  - wherein $R_7$ and $R_8$ independently represent
    - a hydrogen atom,
    - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, or $C_1$-$C_6$ alkylpiperidinium An$^-$;
    - $R_7$ and $R_8$ may form, together with the nitrogen to which they are attached, a cationic or non-cationic, 4- to 7-membered, heterocycle which may contain one or more nitrogen, oxygen or sulfur atoms and which may itself be substituted with one or more radicals, which may be identical or different, selected from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium, or linear or branched $C_1$-$C_6$ alkyl,
- $R_6$ represents:
  - a hydrogen atom,
  - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An$^-$, $C_1$-$C_6$ alkylimidazolium An$^-$, $C_1$-$C_6$ alkylpyridinium An$^-$, or $C_1$-$C_6$ alkylpiperidinium An$^-$,
  - a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri (hydroxy)alkylammonium An⁻, C₁-C₆ alkylimidazolium An⁻, C₁-C₆ alkylpyridinium An⁻, or C₁-C₆ alkylpiperidinium An⁻,
a halide,
a hydroxyl radical,
a radical —NR₉R₁₀,
wherein R₉ and R₁₀ independently represent
a hydrogen atom,
a linear or branched C₁-C₆ alkyl radical which may be substituted with one or more radicals, which may be identical or different, selected from hydroxyls, amino, C₁-C₆ mono(hydroxy)alkylamino or di(hydroxy)alkylamino, C₁-C₆ alkylimidazole, C₁-C₆ tri(hydroxy)alkylammonium An⁻, C₁-C₆ alkylimidazolium An⁻, C₁-C₆ alkylpyridinium An⁻, C₁-C₆ alkylpiperidinium An⁻, or linear or branched C₁-C₆ alkyl
R9 and R10 may form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals. which may be identical or different, selected from hydroxyl, amino, C₁-C₆ mono(hydroxy)alkylamino, C₁-C₆ di(hydroxy)alkylamino C₁-C₆ alkoxy, C₁-C₆ tri(hydroxy)alkylammonium, C₁-C₆ alkylimidazolium, C₁-C₆ alkylpyridinium, or linear or branched C₁-C₆ alkyl,
X represents:
a hydroxyl radical,
a linear or branched C₁-C₆ alkoxy radical which may be substituted with one or more radicals, which may be identical or different, selected from hydroxyls, amino, C₁-C₆ mono(hydroxy)alkylamino or di(hydroxy)alkylamino, C₁-C₆ alkylimidazole, C₁-C₆ tri(hydroxy)alkylammonium An⁻, C₁-C₆ alkylimidazolium An⁻, C₁-C₆ alkylpyridinium An⁻, or C₁-C₆ alkylpiperidinium An⁻;
a radical —NR₁₁R₁₂,
wherein R₁₁ and R₁₂ independently represent
a hydrogen atom,
a linear or branched C₁-C₆ alkyl radical which may be substituted with one or more radicals, which may be identical or different, selected from hydroxyls, amino, C₁-C₆ mono(hydroxy)alkylamino or di(hydroxy)alkylamino, linear or branched C₁-C₆ alkyl, C₁-C₆ alkylimidazole, C₁-C₆ tri(hydroxy)alkylammonium An⁻, C₁-C₆ alkylimidazolium An⁻, C₁-C₆ alkylpyridinium An⁻, or C₁-C₆ alkylpiperidinium An⁻,
R₁₁ and R12 may form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals, which may be identical or different, selected from hydroxyl, amino, C₁-C₆ mono(hydroxy)alkylamino, C₁-C₆ di(hydroxy)alkylamino C₁-C₆ alkoxy, tri(hydroxy)alkylammonium, C₁-C₆ alkylimidazolium, C₁-C₆ alkylpyridinium, or linear or branched C₁-C₆ alkyl, wherein when the compound of formula (I) is positively charged, then it comprises as many anionic counterion(s) An⁻ as cationic charge(s) to achieve the electrical neutrality of the molecule.

16. The composition as claimed in claim 15, comprising one or more oxidizing agents.

17. A process for dyeing keratin fibers, comprising applying to these fibers a composition comprising a compound of formula (I) below, an optical isomer, a geometrical isomer or tautomers thereof, a salt thereof with an acid or a base, or a solvate thereof:

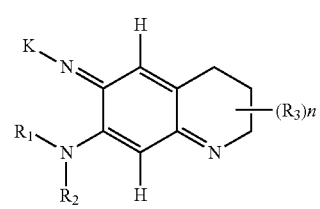

(I)

wherein:
n represents an integer equal to 0, wherein positions not substituted with a radical R₃ carry a hydrogen atom,
R₁ and R₂ represent
a hydrogen atom
R₃ represents:
a linear or branched C₁-C₆ alkyl radical which may be substituted with one or more radicals, which may be identical or different, selected from hydroxyls, amino, C₁-C₆ mono(hydroxy)alkylamino or di(hydroxy)alkylamino, C₁-C₆ alkylimidazole, C₁-C₆ tri (hydroxy)alkylammonium An⁻, C₁-C₆ alkylimidazolium An⁻, C₁-C₆ alkylpyridinium An⁻, or C₁-C₆ alkylpiperidinium An⁻;
K represents a radical corresponding to general formulae (II) to (IV) below:

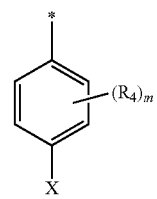

(II)

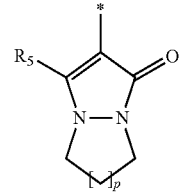

(III)

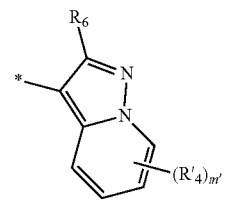

(IV)

wherein:
m represents an integer equal to 0, 1, 2, 3 or 4, wherein positions not substituted with a radical R₄ carry a hydrogen atom,
m' represents an integer equal to 0, 1, 2, 3 or 4, wherein positions not substituted with a radical R'₄ carry a hydrogen atom, p represents an integer equal to 0, 1, 2, 3 or 4, $R_4$ represents:
- a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
- a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
- a halide, $R'_4$ represents:
- a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻,
- a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
- a halide, $R_5$ represents:
- a hydrogen atom,
- a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
- a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻,
- a halide,
- a hydroxyl radical,
- a radical —$NR_7R_8$,
  wherein $R_7$ and $R_8$ independently represent
  - a hydrogen atom,
  - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
  - $R_7$ and $R_8$ may form, together with the nitrogen to which they are attached, a cationic or non-cationic, 4- to 7-membered, heterocycle which may contain one or more nitrogen, oxygen or sulfur atoms and which may itself be substituted with one or more radicals, which may be identical or different, selected from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium, or linear or branched $C_1$-$C_6$ alkyl, $R_6$ represents:
- a hydrogen atom,
- a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻,
- a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻,
- a halide,
- a hydroxyl radical,
- a radical —$NR_9R_{10}$,
  wherein $R_9$ and $R_{10}$ independently represent
  - a hydrogen atom,
  - a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, $C_1$-$C_6$ alkylpiperidinium An⁻, or linear or branched $C_1$-$C_6$ alkyl,
- $R_9$ and $R_{10}$ may form, together with the nitrogen to which they are attached, a cationic or non-cationic, 4- to 7-membered. non-aromatic heterocycle which may contain one or more nitrogen, oxygen or sulfur atoms and which may itself be substituted with one or more radicals, which may be identical or different, selected from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium, or linear or branched $C_1$-$C_6$ alkyl, X represents:
- a hydroxyl radical,
- a linear or branched $C_1$-$C_6$ alkoxy radical which may be substituted with one or more radicals, which may be identical or different, selected from hydroxyls, amino, $C_1$-$C_6$ mono(hydroxy)alkylamino or di(hydroxy)alkylamino, $C_1$-$C_6$ alkylimidazole, $C_1$-$C_6$ tri(hydroxy)alkylammonium An⁻, $C_1$-$C_6$ alkylimidazolium An⁻, $C_1$-$C_6$ alkylpyridinium An⁻, or $C_1$-$C_6$ alkylpiperidinium An⁻;
- a radical —$NR_{11}R_{12}$, wherein $R_{11}$ and $R_{12}$ independently represent
  a hydrogen atom,
  a linear or branched $C_1$-$C_6$ alkyl radical which may be substituted with one or more radicals, which may be identical or different, selected from hydroxyls, amino, $C_1$-$C_6$ mono(hydroxy)alkylamino or di(hydroxy)alkylamino, linear or branched $C_1$-$C_6$ alkyl, $C_1$-$C_6$ alkylimidazole, $C_1$-$C_6$ tri(hydroxy)alkylammonium $An^-$, $C_1$-$C_6$ alkylimidazolium $An^-$, $C_1$-$C_6$ alkylpyridinium $An^-$, or $C_1$-$C_6$ alkylpiperidinium $An^-$,
$R_{11}$ and $R_{12}$ may form, together with the nitrogen to which they are attached, a cationic or non-cationic, 4- to 7-membered, non-aromatic heterocycle which may contain one or more nitrogen, oxygen or sulfur atoms and which may itself be substituted with one or more radicals, which may be identical or different, selected from hydroxyl, amino, $C_1$-$C_6$ mono(hydroxy)alkylamino, $C_1$-$C_6$ di(hydroxy)alkylamino $C_1$-$C_6$ alkoxy, $C_1$-$C_6$ tri(hydroxy)alkylammonium, $C_1$-$C_6$ alkylimidazolium, $C_1$-$C_6$ alkylpyridinium, or linear or branched $C_1$-$C_6$ alkyl,
wherein when the compound of formula (I) is positively charged, then it comprises as many anionic counterion(s) $An^-$ as cationic charge(s) to achieve the electrical neutrality of the molecule.

\* \* \* \* \*

UNITED STATES PATENT AND TRADEMARK OFFICE
CERTIFICATE OF CORRECTION

PATENT NO. : 11,117,864 B2
APPLICATION NO. : 16/310974
DATED : September 14, 2021
INVENTOR(S) : Sabelle et al.

Page 1 of 1

It is certified that error appears in the above-identified patent and that said Letters Patent is hereby corrected as shown below:

In the Claims

Column 30, Claim 11, Line 14, after "tri(hydroxy)alkylammonium," insert -- $C_1$-$C_6$ --;

Column 30, Claim 12, Line 18, change "R12" to -- $R_{12}$ --; and

Column 35, Claim 15, Line 60, before "tri(hydroxy)alkylammonium," insert -- $C_1$-$C_6$ --.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*